(12) United States Patent
Mese et al.

(10) Patent No.: US 11,558,848 B2
(45) Date of Patent: Jan. 17, 2023

(54) INTELLIGENT NOTIFICATION DELIVERY

(71) Applicant: Lenovo (Singapore) Pte. Ltd., Singapore (SG)

(72) Inventors: John Carl Mese, Cary, NC (US); Scott Edwards Kelso, Cary, NC (US); Aaron Michael Stewart, Raleigh, NC (US); Russell Speight VanBlon, Raleigh, NC (US); Nathan J. Peterson, Oxford, NC (US); Arnold S. Weksler, Raleigh, NC (US)

(73) Assignee: Lenovo (Singapore) Pte. Ltd., Singapore (SG)

(*) Notice: Subject to any disclaimer, the term of this patent is extended or adjusted under 35 U.S.C. 154(b) by 84 days.

(21) Appl. No.: 15/085,437

(22) Filed: Mar. 30, 2016

(65) Prior Publication Data

US 2017/0289954 A1 Oct. 5, 2017

(51) Int. Cl.
*H04W 68/00* (2009.01)
*H04W 4/021* (2018.01)
*A61B 7/04* (2006.01)
*H04W 4/70* (2018.01)
*H04W 4/80* (2018.01)
(Continued)

(52) U.S. Cl.
CPC ............ *H04W 68/00* (2013.01); *A61B 7/04* (2013.01); *H04W 4/021* (2013.01); *H04W 4/70* (2018.02); *H04W 4/80* (2018.02); *A61B 5/0077* (2013.01); *A61B 5/389* (2021.01); *A61B 2562/0204* (2013.01)

(58) Field of Classification Search
CPC ....... H04L 67/18; H04L 67/24; H04L 67/306; H04L 61/2038; H04L 63/20; H04L 69/18; H04L 63/0492; H04W 4/02; H04W 4/008; H04W 4/206; H04W 8/005; H04W 4/028; H04W 68/00; H04W 4/005; H04W 4/021; G06Q 50/01; H04M 2242/30; H04M 2203/2094; H04M 3/42357; H04M 2250/12; H04M 1/6033
See application file for complete search history.

(56) References Cited

U.S. PATENT DOCUMENTS

2006/0093998 A1* 5/2006 Vertegaal ............... G06F 3/011
434/236
2009/0305744 A1* 12/2009 Ullrich .............. H04M 1/72569
455/567
(Continued)

FOREIGN PATENT DOCUMENTS

CA 3015104 A1 * 5/2014 ............ G06F 21/30

*Primary Examiner* — Srilakshmi K Kumar
*Assistant Examiner* — Jing Gao
(74) *Attorney, Agent, or Firm* — Ference & Associates LLC

(57) ABSTRACT

One embodiment provides a method, including: detecting, at an electronic device, an event has occurred; detecting, using a device sensor, that the electronic device is proximate to at least one other person; accessing, in a storage location, a rule set including a rule regarding the detecting that the electronic device is proximate to at least one other person; identifying, using a processor of the electronic device, a type of notification for the event based on the rule set; and providing, using an output device of the electronic device, a notification of the type identified. Other aspects are described and claimed.

14 Claims, 3 Drawing Sheets

(51) Int. Cl.
  *A61B 5/00*    (2006.01)
  *A61B 5/389*   (2021.01)

(56) References Cited

U.S. PATENT DOCUMENTS

| | | | |
|---|---|---|---|
| 2011/0177802 A1* | 7/2011 | Gupta | H04L 12/66 455/418 |
| 2012/0214461 A1* | 8/2012 | Raghavan | H04M 1/72569 455/418 |
| 2015/0207916 A1* | 7/2015 | Xue | H04W 4/12 455/412.2 |

* cited by examiner

INTELLIGENT NOTIFICATION DELIVERY

BACKGROUND

Information handling devices ("devices" or "electronic devices"), for example laptop computers, smart phones, tablet devices, smart watches and other wearables, and the like, are utilized for communication. Common examples include voice calls, text messaging, instant messaging, in-application messaging, video calls, etc. Such devices also provide the user with notifications regarding updates in social media applications, news applications, etc.

Event notifications, whether a notification of a live call (such as a voice or video call) being received or a notification that a message has been received at the device (e.g., text message, email, social media application update, etc.) are provided to the device user, typically in an automated fashion in real time. Different modes of notification may be provided, for example audible notifications, on-screen notifications, visible notifications, haptic notifications such as device vibrations, etc.

A user may select a default mode for a notification, e.g., based on application type, device contact, or globally, e.g., via switch (software or hardware). For example, a user might select a particular type of audible notification for a given device contact, application, or message type. Similarly, a device user may select to only receive haptic feedback but not audible feedback from all contacts and for all applications, messages, etc., such as by operating a hardware switch or updating a setting in the device notification settings.

BRIEF SUMMARY

In summary, one aspect provides a method, comprising: detecting, at an electronic device, an event has occurred; detecting, using a device sensor, that the electronic device is proximate to at least one other person; accessing, in a storage location, a rule set comprising a rule regarding the detecting that the electronic device is proximate to at least one other person; identifying, using a processor of the electronic device, a type of notification for the event based on the rule set; and providing, using an output device of the electronic device, a notification of the type identified.

Another aspect provides a system, comprising: a device sensor; a processor operatively coupled to the device sensor; and a memory device that stores instructions executable by the processor to: detect an event has occurred; detect, using the device sensor, that a user of the electronic device is proximate to at least one other person; access a rule set comprising a rule regarding the detection that the electronic device is proximate to at least one other person; identify a type of notification for the event based on the rule set; and provide a notification of the type identified.

A further aspect provides a product, comprising: a storage device having code stored therewith, the code being executable by a processor and comprising: code that detects, at an electronic device, an event has occurred; code that detects, using a device sensor, that a user of the electronic device is proximate to at least one other person; code that accesses, in a storage location, a rule set comprising a rule regarding the detection that the electronic device is proximate to at least one other person; code that identifies, using a processor of the electronic device, a type of notification for the event based on the rule set; and code that provides, using an output device of the electronic device, a notification of the type identified.

The foregoing is a summary and thus may contain simplifications, generalizations, and omissions of detail; consequently, those skilled in the art will appreciate that the summary is illustrative only and is not intended to be in any way limiting.

For a better understanding of the embodiments, together with other and further features and advantages thereof, reference is made to the following description, taken in conjunction with the accompanying drawings. The scope of the invention will be pointed out in the appended claims.

DETAILED DESCRIPTION

Figure 1:
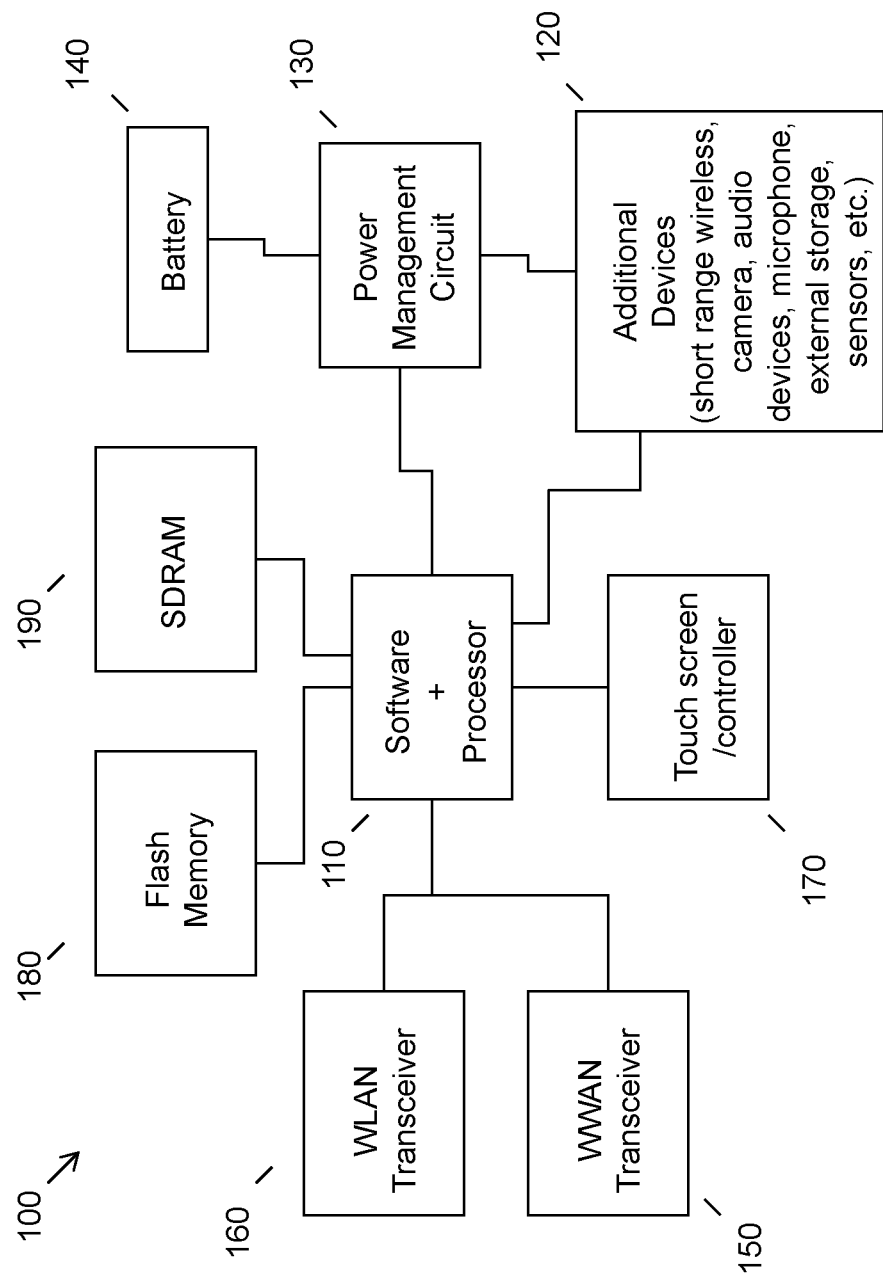
FIG. 1 illustrates an example of information handling device circuitry.

It will be readily understood that the components of the embodiments, as generally described and illustrated in the figures herein, may be arranged and designed in a wide variety of different configurations in addition to the described example embodiments. Thus, the following more detailed description of the example embodiments, as represented in the figures, is not intended to limit the scope of the embodiments, as claimed, but is merely representative of example embodiments.

Reference throughout this specification to "one embodiment" or "an embodiment" (or the like) means that a particular feature, structure, or characteristic described in connection with the embodiment is included in at least one embodiment. Thus, the appearance of the phrases "in one embodiment" or "in an embodiment" or the like in various places throughout this specification are not necessarily all referring to the same embodiment.

Furthermore, the described features, structures, or characteristics may be combined in any suitable manner in one or more embodiments. In the following description, numerous specific details are provided to give a thorough understanding of embodiments. One skilled in the relevant art will recognize, however, that the various embodiments can be practiced without one or more of the specific details, or with other methods, components, materials, et cetera. In other instances, well known structures, materials, or operations are not shown or described in detail to avoid obfuscation.

Device notifications can interrupt human interactions. An event such as an incoming text message or a detected application status update received at a user's phone, for example, might cause a user engaged in conversation with another person to stop talking momentarily to look at his or her device (e.g., smart phone, smart watch, etc.). This is especially true for wearable devices, like a smart watch. This modern convenience of instant event notification is sometimes disruptive. What is needed is a dynamic way to better identify when or how to deliver such notifications.

While conventional techniques apply global settings that allow a user to suppress notifications altogether, or to only allow user-defined priority notifications or notification types, such techniques require a user to take overt action. Moreover, such techniques are based on proactive user implemented settings, i.e., the user must proactively modify notification settings in order to accomplish anything other than receiving a default notification or last-set notification type. Thus, a user must change notification settings to silence all notifications, to change a particular device contact's notification to a given setting, etc. While many notification options are therefore currently available to device users, most users find the notification settings interface challenging to master and, even if a user is comfortable adjusting the notification settings, such user is often not capable of accurately predicting many device notification contexts ahead of time.

Accordingly, an embodiment detects if the device user is interacting with other people in order to intelligently modify a notification type. This modification of a type of the notification may include changing an amplitude of a notification, changing a mode of the notification (e.g., audible versus visible notifications), or even changing the timing of the notification, e.g., determining that the notification should be delayed until a later time.

An embodiment may detect if the user is interacting with other(s) in a variety of ways. For example, an embodiment may consult a rule set that is used to determine if the user is currently interacting with at least on other person. The rule set may include a rule regarding detected location, e.g., at home or at the office versus travelling or out at a restaurant, in order to determine if the user is likely to be interacting with at least one other person and thus likely not wanting a notification (or a particular type of notification).

An embodiment may employ biometric identification, e.g., use of voice or other biometric data like electromyography (EMG) data or sub-audible data, to detect if the device user is currently interacting with another person and/or interacting with a particular person. For example, an embodiment may employ biometric data to identify that the device user is an active participant in a conversation as opposed to just being in a crowd (such as on a bus or a plane).

An embodiment may detect nearby devices (e.g., personal devices such as phones, tablets, wearables, etc., and/or other devices such as network devices and the like) that in turn may provide data to uniquely identify people with whom the device user is interacting. Thus, an embodiment may modify a notification based on a particular person with which the device user is interacting.

In an embodiment, the decision as to whether to provide a notification may apply a machine learning technique to improve the decisions over time. For example, an embodiment may determine the relative importance of people around the device user in an effort to ascertain if a particular notification should be provided at a particular time or in a particular way. By way of example, if the device is near Person A and the device user ignores a notification from Person X, then this data may later be used in learning not to notify the device user for that type of message (e.g., from Person X) when the device user is around Person A.

In contrast, if the device detects that it is near Person B (e.g., detects Person B via biometric data and/or detects Person B's device nearby) and the device user reads a notification from Person Y, then an embodiment learns to notify the device user for that type of message (e.g., from Person Y) when the device user is around Person B. Over time, an embodiment learns from the types of messages, nearby people, and senders of messages to determine if some senders or messages should never interrupt, while an embodiment may learn that other senders (e.g., a high priority contact) may always interrupt. For example, an embodiment may build a prioritized list for notification types and people so as to more intelligently handle future messages.

In an embodiment, the decision to provide a type of notification may also include a determination of how the notification is delivered. For example, whether to make a sound or vibration type of notification, e.g., based on the event type (email message, voice call, etc.) and which other person(s) is/are in close proximity. The notification may be delivered to a sub-audible device, such as a headset, ear piece, or implant, such that only the particular device user to be notified would even be aware that a notification was delivered. This avoids disruption to a conversation. This type of decision technique may be part of a hierarchy that maps a notification's priority with the proper type of delivery.

Time of day also may govern or influence if and/or how a notification is provided. Additionally, the state of nearby devices may be factored into the decision process. For example, if a nearby device is detected, but that device is in use (e.g., playing a video, etc.), this may counsel a decision that the device user is not engaged in active conversation, and thus the notification delivery is less likely to be viewed as an interruption.

In an embodiment, an override (such as a predetermined gesture) may be used to allow a device user to postpone a notification that is provided but still is viewed as an interruption. This user response to the unwanted notification may be stored and used to modify the notification rule or rules used to provide the notification (and/or others) under these circumstances.

The illustrated example embodiments will be best understood by reference to the figures. The following description is intended only by way of example, and simply illustrates certain example embodiments.

While various other circuits, circuitry or components may be utilized in information handling devices, with regard to smart phone and/or tablet circuitry 100, an example illustrated in FIG. 1 includes a system on a chip design found for example in tablet or other mobile computing platforms. Software and processor(s) are combined in a single chip 110. Processors comprise internal arithmetic units, registers, cache memory, busses, I/O ports, etc., as is well known in the art. Internal busses and the like depend on different vendors, but essentially all the peripheral devices (120) may attach to a single chip 110. The circuitry 100 combines the processor, memory control, and I/O controller hub all into a single chip 110. Also, systems 100 of this type do not typically use SATA or PCI or LPC. Common interfaces, for example, include SDIO and I2C.

There are power management chip(s) 130, e.g., a battery management unit, BMU, which manage power as supplied, for example, via a rechargeable battery 140, which may be recharged by a connection to a power source (not shown). In at least one design, a single chip, such as 110, is used to supply BIOS like functionality and DRAM memory.

System 100 typically includes one or more of a WWAN transceiver 150 and a WLAN transceiver 160 for connecting to various networks, such as telecommunications networks and wireless Internet devices, e.g., access points. Additionally, devices 120 are commonly included, e.g., an image sensor (e.g., a camera), a short range wireless device for communicating with other devices, and the like. System 100 often includes a touch screen 170 for data input and display/rendering. System 100 also typically includes various memory devices, for example flash memory 180 and SDRAM 190.

Figure 2:
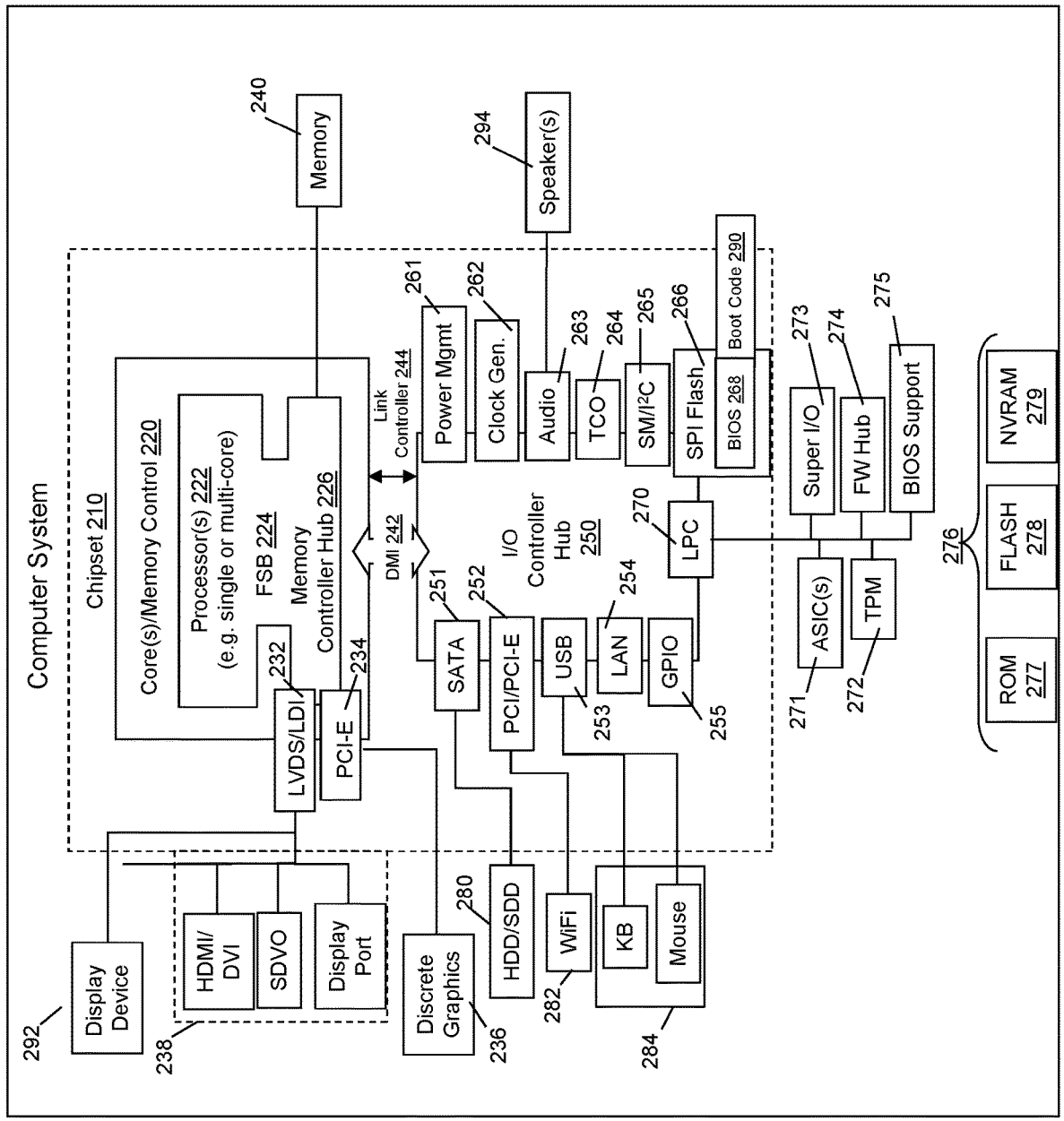
FIG. 2 illustrates another example of information handling device circuitry.

FIG. 2 depicts a block diagram of another example of information handling device circuits, circuitry or components. The example depicted in FIG. 2 may correspond to computing systems such as the THINKPAD series of personal computers sold by Lenovo (US) Inc. of Morrisville, N.C., or other devices. As is apparent from the description herein, embodiments may include other features or only some of the features of the example illustrated in FIG. 2.

The example of FIG. 2 includes a so-called chipset 210 (a group of integrated circuits, or chips, that work together, chipsets) with an architecture that may vary depending on manufacturer (for example, INTEL, AMD, ARM, etc.). INTEL is a registered trademark of Intel Corporation in the United States and other countries. AMD is a registered trademark of Advanced Micro Devices, Inc. in the United States and other countries. ARM is an unregistered trademark of ARM Holdings plc in the United States and other countries. The architecture of the chipset 210 includes a core and memory control group 220 and an I/O controller hub 250 that exchanges information (for example, data, signals, commands, etc.) via a direct management interface (DMI) 242 or a link controller 244. In FIG. 2, the DMI 242 is a chip-to-chip interface (sometimes referred to as being a link between a "northbridge" and a "southbridge"). The core and memory control group 220 include one or more processors 222 (for example, single or multi-core) and a memory controller hub 226 that exchange information via a front side bus (FSB) 224; noting that components of the group 220 may be integrated in a chip that supplants the conventional "northbridge" style architecture. One or more processors 222 comprise internal arithmetic units, registers, cache memory, busses, I/O ports, etc., as is well known in the art.

In FIG. 2, the memory controller hub 226 interfaces with memory 240 (for example, to provide support for a type of RAM that may be referred to as "system memory" or "memory"). The memory controller hub 226 further includes a low voltage differential signaling (LVDS) interface 232 for a display device 292 (for example, a CRT, a flat panel, touch screen, etc.). A block 238 includes some technologies that may be supported via the LVDS interface 232 (for example, serial digital video, HDMI/DVI, display port). The memory controller hub 226 also includes a PCI-express interface (PCI-E) 234 that may support discrete graphics 236.

In FIG. 2, the I/O hub controller 250 includes a SATA interface 251 (for example, for HDDs, SDDs, etc., 280), a PCI-E interface 252 (for example, for wireless connections 282), a USB interface 253 (for example, for devices 284 such as a digitizer, keyboard, mice, cameras, phones, microphones, storage, other connected devices, etc.), a network interface 254 (for example, LAN), a GPIO interface 255, a LPC interface 270 (for ASICs 271, a TPM 272, a super I/O 273, a firmware hub 274, BIOS support 275 as well as various types of memory 276 such as ROM 277, Flash 278, and NVRAM 279), a power management interface 261, a clock generator interface 262, an audio interface 263 (for example, for speakers 294), a TCO interface 264, a system management bus interface 265, and SPI Flash 266, which can include BIOS 268 and boot code 290. The I/O hub controller 250 may include gigabit Ethernet support.

The system, upon power on, may be configured to execute boot code 290 for the BIOS 268, as stored within the SPI Flash 266, and thereafter processes data under the control of one or more operating systems and application software (for example, stored in system memory 240). An operating system may be stored in any of a variety of locations and accessed, for example, according to instructions of the BIOS 268. As described herein, a device may include fewer or more features than shown in the system of FIG. 2.

Information handling device circuitry, as for example outlined in FIG. 1 or FIG. 2, may be used in devices that provide a user with notifications in response to events such as messages that are received by the user's device or devices. For example, a device such as a laptop computer may include circuitry such as outlined in FIG. 1, whereas a user's smart phone may include circuitry such as outlined in FIG. 2. These devices may in some cases cooperate to notify a user of an event, e.g., an event notification may be passed from a user's laptop (or other device such as a smart phone) to another user device (such as a wearable device, e.g., a smart watch). Other data, e.g., sensed data such as location data, biometric data, etc., may also be communicated between user devices, as further described herein.

Figure 3:
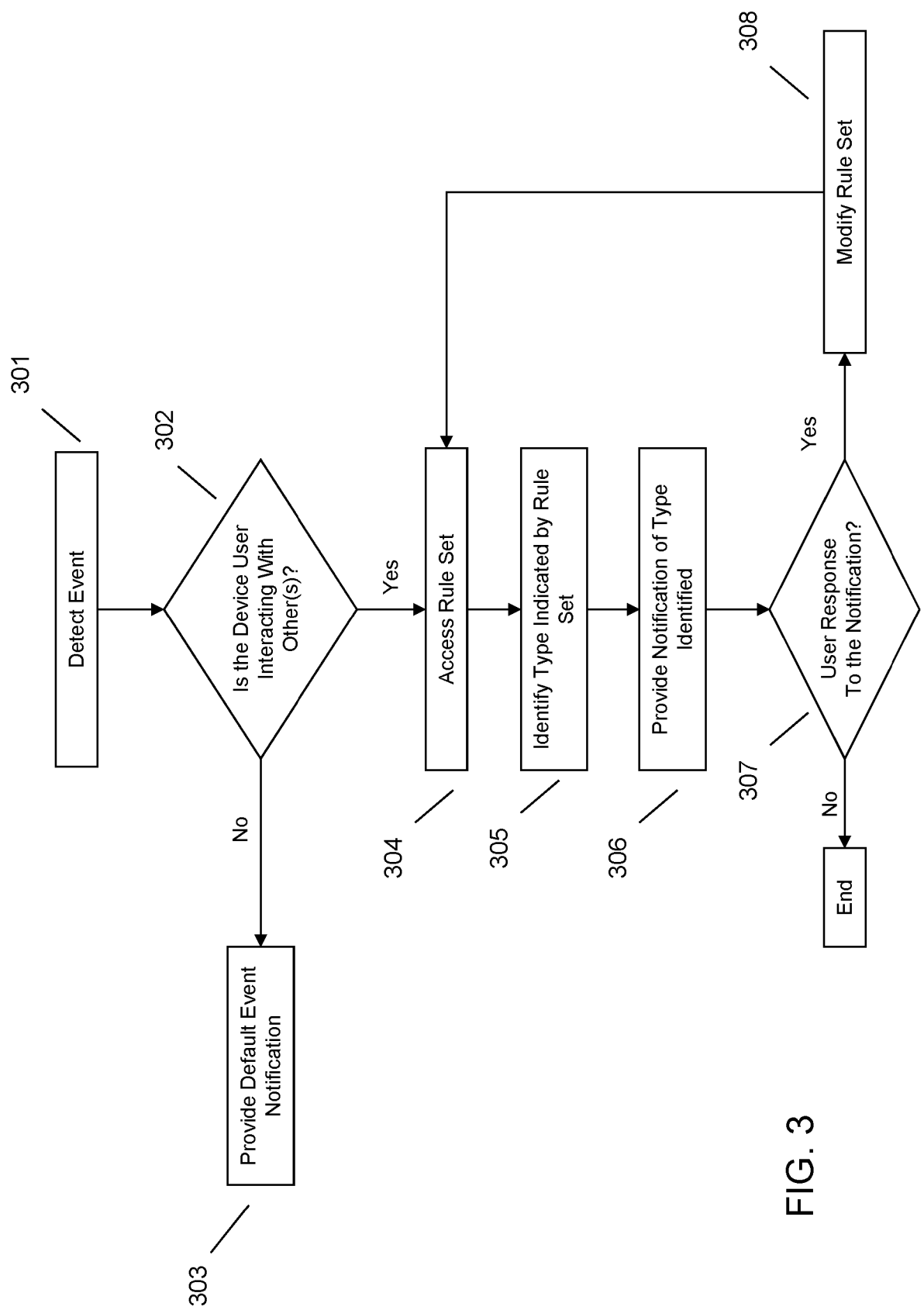
FIG. 3 illustrates an example method of intelligent notification delivery according to an embodiment.

FIG. 3 illustrates an example method of intelligent notification delivery based on a determination of whether the user is interacting with at least one other person. As shown, at 301 an event is detected. For example, a social media application running on a first user's device (herein, User A) may determine a notification is appropriate, i.e., in response to a message received, an in-application event, etc. Typically, this would result in a notification being produced for the event according to a default rule for the device (e.g., smart phone, smart watch, etc.). By way of example, often such an event causes the device to light an LED and/or produce a vibration or an audible chime. While each of these notification types or modes is minimally intrusive, each may also cause the User A to be interrupted in an unwelcome way, particularly if User A is interacting with another person when the notification is generated and delivered.

Thus, rather than issuing a stock of default notification without regard to User A's activity or surroundings, an embodiment determines at 302 if User A is interacting with at least one other person at 302.

As has been described herein, this interaction state determination may be accomplished using a variety of techniques. For example, step 302 may include User A's device using a sensor such as a short range wireless communication device, an RFID device, a near field device, etc., to detect another device, e.g., that of a known user (User B herein). Such device detection may be used to infer that User A is interacting with User B due to User B's proximately located device. As another example, step 302 may include using a device sensor of User A's device to detect a person, e.g., User B. For example, the device sensor of User A's device may be used to collect biometric data selected from the group consisting of microphone data and camera data in order to detect User B. As a further example, step 302 may include a process by which a device sensor of User A's device is used to detect a geographic location, e.g., by way of accessing data from a GPS service. This location detection may be used to infer that User A is in a location in which the user is highly likely (or highly unlikely) to be interacting with another person. If no interaction is detected, a default notification mechanism may be employed at 303.

At 304, however, an embodiment may access a rule set that includes at least one rule regarding the user (here, User A) interacting with at least one other person (e.g., User B or any other person or persons generally) in response to the determination that User A is interacting with at least one other person. An embodiment utilizes the rule set at 305 to identify a type of notification that should be used in the particular context detected. For example, an embodiment may determine that User A is interacting with another user, e.g., User B. The rule set may indicate that 1) when User A is interacting with anyone (generally), a notification of a visual type should be used, rather than an audible notification. Furthermore, the rule set may indicate that 2) when User A is interacting with User B (specifically), a haptic or vibration based notification should be used, rather than a visual or an audible notification.

An embodiment may thus provide a notification of the type identified using the rule set at 306. In the foregoing example, an embodiment would provide a haptic or vibration based notification to a social media application generated event, rather than an audible or a visual notification, or other existing default notification type, if any, when User B's device is detected at a relevant time, i.e., during notification generation and/or delivery.

If a user response to the notification is determined at 307, an embodiment may modify the rule set based on the user response, as illustrated at 308. By way of example, if User A receives a haptic or vibratory notification of a social media application generated event, while interacting with User B, and User A operates his or her device to open that social media application to check the notification within a predetermined time of the notification, this may act as positive feedback to enforce the confidence of the decision made to send the notification. Likewise, if User A performs an override gesture to mute or discontinue the haptic or vibratory notification, this may act as negative feedback, e.g., altering the rule set to make a different choice when faced with this scenario in the future.

Therefore, an embodiment represents a technical improvement to device notification delivery. In an embodiment, default notifications may be modified (changed, delayed, cancelled) to avoid interrupting a user that is currently interacting with at least one other person. If a context is sensed by a user's device that an interaction is likely, an embodiment acts to modify a default notification without requiring the user to manually adjust the notification settings. Moreover, an embodiment tracks the reaction of the user to the notifications over time such that machine learning may be applied to improve the future delivery of notifications, e.g., their type, timing and the like.

As will be appreciated by one skilled in the art, various aspects may be embodied as a system, method or device program product. Accordingly, aspects may take the form of an entirely hardware embodiment or an embodiment including software that may all generally be referred to herein as a "circuit," "module" or "system." Furthermore, aspects may take the form of a device program product embodied in one or more device readable medium(s) having device readable program code embodied therewith.

It should be noted that the various functions described herein may be implemented using instructions stored on a device readable storage medium such as a non-signal storage device that are executed by a processor. A storage device may be, for example, an electronic, magnetic, optical, electromagnetic, infrared, or semiconductor system, apparatus, or device, or any suitable combination of the foregoing. More specific examples of a storage medium would include the following: a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a storage device is not a signal and "non-transitory" includes all media except signal media.

Program code embodied on a storage medium may be transmitted using any appropriate medium, including but not limited to wireless, wireline, optical fiber cable, RF, et cetera, or any suitable combination of the foregoing.

Program code for carrying out operations may be written in any combination of one or more programming languages. The program code may execute entirely on a single device, partly on a single device, as a stand-alone software package, partly on single device and partly on another device, or entirely on the other device. In some cases, the devices may be connected through any type of connection or network, including a local area network (LAN) or a wide area network (WAN), or the connection may be made through other devices (for example, through the Internet using an Internet Service Provider), through wireless connections, e.g., near-field communication, or through a hard wire connection, such as over a USB connection.

Example embodiments are described herein with reference to the figures, which illustrate example methods, devices and program products according to various example embodiments. It will be understood that the actions and functionality may be implemented at least in part by program instructions. These program instructions may be provided to a processor of a device, a special purpose information handling device, or other programmable data processing device to produce a machine, such that the instructions, which execute via a processor of the device implement the functions/acts specified.

It is worth noting that while specific blocks are used in the figures, and a particular ordering of blocks has been illustrated, these are non-limiting examples. In certain contexts, two or more blocks may be combined, a block may be split into two or more blocks, or certain blocks may be re-ordered or re-organized as appropriate, as the explicit illustrated examples are used only for descriptive purposes and are not to be construed as limiting.

As used herein, the singular "a" and "an" may be construed as including the plural "one or more" unless clearly indicated otherwise.

This disclosure has been presented for purposes of illustration and description but is not intended to be exhaustive or limiting. Many modifications and variations will be apparent to those of ordinary skill in the art. The example embodiments were chosen and described in order to explain principles and practical application, and to enable others of ordinary skill in the art to understand the disclosure for various embodiments with various modifications as are suited to the particular use contemplated.

Thus, although illustrative example embodiments have been described herein with reference to the accompanying figures, it is to be understood that this description is not limiting and that various other changes and modifications may be affected therein by one skilled in the art without departing from the scope or spirit of the disclosure.

What is claimed is:

1. A method, comprising:

detecting, at an electronic device, an event has occurred;

detecting, using one or more device sensors, that a user of the electronic device is interacting with at least one other person based upon a proximity of the at least one other person to the user, wherein the detecting that the user of the electronic device is interacting with the at least one other person comprises determining, from the one or more device sensors, an interaction state of the user with the at least one other person and an identity of the at least one other person, wherein the determining the identity of the at least one other person comprises utilizing the one or more device sensors to collect biometric data associated with the at least one other person, wherein the device sensor is used to collect biometric data selected from the group consisting of electromyography data, sub-audible data, microphone data, and camera data;

identifying, using a processor of the electronic device, a type of notification for the event based on a rule set comprising a rule regarding the user of the electronic device interacting with at least one other person, wherein the type of notification identified for provision is based upon the interaction state of the user with the at least one other person and the identity of the at least one other person, wherein the type of notification is altered from an initial setting based upon the interaction state of the user with the at least one other person and is further modified based upon the identity of the at least one other person, wherein the type of notification for the event, based on the rule set, is changed from a default type of notification to a modified type of notification selected in the rule set based on the identity of the at least one other person and the interaction state of the user with the at least one other person; and providing, using an output device of the electronic device, the modified type of notification identified to the user.

2. The method of claim 1, further comprising:
determining a user response to the notification; and
modifying the rule set based on the user response.

3. The method of claim 1, wherein the device sensor is used to detect another device;
wherein the type of notification is modified based on the detection of a particular device identified in the rule set.

4. The method of claim 3, wherein the type of notification for the event based on the rule set is changed from a default type selected in the rule set based on the detection of the particular device.

5. The method of claim 1, wherein the device sensor is used to detect a geographic location;
wherein the type of notification is modified based on the detection of a particular geographic location identified in the rule set.

6. The method of claim 2, wherein the event comprises a message being received, and wherein the determining a user response to the notification comprises detecting that the message has been opened.

7. The method of claim 1, further comprising overriding the notification in response to user input.

8. A system, comprising:
one or more device sensors;
a processor operatively coupled to the one or more device sensors; and
a memory device that stores instructions executable by the processor to:
detect an event has occurred;
detect, using the one or more device sensors, that a user of the electronic device is interacting with at least one other person based upon a proximity of the at least one other person to the user, wherein to detect that the user of the electronic device is interacting with the at least one other person comprises to determine, from the one or more device sensors, an interaction state of the user with the at least one other person and an identity of the at least one other person, wherein the determining the identity of the at least one other person comprises utilizing the one or more device sensors to collect biometric data associated with the at least one other person, wherein the device sensor is used to collect biometric data selected from the group consisting of electromyography data, sub-audible data, microphone data, and camera data;

identify a type of notification for the event based on a rule set comprising a rule regarding the user of the electronic device is interacting with at least one other person, wherein the type of notification identified for provision is based upon the interaction state of the user with the at least one other person and the identity of the at least one other person, wherein the type of notification is altered from an initial setting based upon the interaction state of the user with the at least one other person and is further modified based upon the identity of the at least one other person, wherein the type of notification for the event, based on the rule set, is changed from a default type of notification to a modified type of notification selected in the rule set based on the identity of the at least one other person and the interaction state of the user with the at least one other person; and provide the modified type of notification identified to the user.

9. The system of claim 8, wherein the instructions are executable by the processor to:
determine a user response to the notification; and
modify the rule set based on the user response.

10. The system of claim 8, wherein the device sensor is used to detect another device;
wherein the type of notification is modified based on the detection of a particular device identified in the rule set.

11. The system of claim 10, wherein the type of notification for the event based on the rule set is changed from a default type selected in the rule set based on the detection of the particular device.

12. The system of claim 8, wherein the device sensor is used to detect a geographic location;
wherein the type of notification is modified based on the detection of a particular geographic location identified in the rule set.

13. The system of claim 9, wherein the event comprises a message being received, and wherein the instructions that determine a user response to the notification comprise instructions that detect that the message has been opened.

14. A product, comprising:
a storage device having code stored therewith, the code being executable by a processor and comprising:
code that detects, at an electronic device, an event has occurred;
code that detects, using one or more device sensors, that a user of the electronic device is interacting with at least one other person based upon a proximity of the at least one other person to the user, wherein the code that detects that the user of the electronic device is interacting with the at least one other person comprises code that determines, from the device sensor, an interaction state of the user with the at least one other person and an identity of the at least one other person, wherein the determining the identity of the at least one other person comprises utilizing the one or more device sensors to collect biometric data associated with the at least one other person, wherein the device sensor is used to collect biometric data selected from the group consisting of electromyography data, sub-audible data, microphone data, and camera data;

code that identifies, using a processor of the electronic device, a type of notification for the event based on a rule set comprising a rule regarding the user of the electronic device is interacting with at least one other person, wherein the type of notification identified for provision is based upon the interaction state of the user with the at least one other person and the identity of the at least one other person, wherein the type of notification is altered from an initial setting based upon the interaction state of the user with the at least one other person and is further modified based upon the identity of the at least one other person, wherein the type of notification for the event, based on the rule set, is changed from a default type of notification to a modified type of notification selected in the rule set based on the identity of the at least one other person and the interaction state of the user with the at least one other person; and code that provides, using an output device of the electronic device, the modified type of notification identified to the user.

* * * * *